United States Patent [19]

Held

[11] Patent Number: 4,778,373
[45] Date of Patent: Oct. 18, 1988

[54] APPARATUS FOR CONTINUOUS HEATED PRESSING OF MATERIAL IN SHEET FORM

[76] Inventor: Kurt Held, Alte Strasse 1, D-7218 Trossingen 2, Fed. Rep. of Germany

[21] Appl. No.: 49,709

[22] Filed: May 13, 1987

Related U.S. Application Data

[62] Division of Ser. No. 730,328, May 3, 1985, Pat. No. 4,693,859.

[30] Foreign Application Priority Data

May 8, 1984 [DE] Fed. Rep. of Germany ....... 3416985

[51] Int. Cl.⁴ ............................................. B29C 43/48
[52] U.S. Cl. ..................... 425/335; 156/555; 156/583.5; 264/347; 264/DIG. 46; 425/371
[58] Field of Search ............... 156/272.2, 380.2, 497, 156/583.5, 62.2, 82, 555; 264/80, 175, 25, 26, 39, 109, 112, 347, DIG. 65, DIG. 46; 425/174.4, 335, 371, 373, 384, 407, 143, 144, 336, 337; 100/93 RP, 151, 153

[56] References Cited

U.S. PATENT DOCUMENTS

| 3,228,062 | 1/1966 | Claus | 425/371 |
| 3,347,697 | 10/1967 | Gmitro | 264/80 |
| 3,361,607 | 1/1968 | Bruno | 264/80 |
| 3,783,062 | 1/1974 | Martin | 264/80 |
| 4,090,902 | 5/1978 | Ferrentino et al. | 156/272.2 |
| 4,283,246 | 8/1981 | Held | 425/371 |
| 4,573,404 | 3/1986 | Held | 425/371 |

FOREIGN PATENT DOCUMENTS

| 1262565 | 3/1968 | Fed. Rep. of Germany | 156/583.5 |
| 564740 | 10/1944 | United Kingdom | 156/497 |
| 2098541A | 10/1982 | United Kingdom | 156/497 |

*Primary Examiner*—Jay H. Woo
*Assistant Examiner*—C. Scott Bushey
*Attorney, Agent, or Firm*—Toren, McGeady & Associates

[57] ABSTRACT

For the continuous pressing of sheet material in a reaction zone between two endless, heated press belts of a double band press at increased process temperatures, the capability for operating at process temperatures which are higher than critical, permissible operating temperatures of the double band press is achieved by heating the press belts in such a way that they have the highest temperature at their outsides facing the sheet material with heat flow through the press belt being effected from the hot outer side to the opposite inner side of the press belt. The heat flow direction in the reaction zone which otherwise leads from a pressure plate to the press belt outer side is thus reversed and, heating members are arranged in the vicinity of the press belt on the outer side thereof shortly before the reaction zone.

3 Claims, 2 Drawing Sheets

APPARATUS FOR CONTINUOUS HEATED PRESSING OF MATERIAL IN SHEET FORM

This is a division of application Ser. No. 730,328 filed May 3, 1985 now U.S. Pat. No. 4,693,859 issued 9-15-87.

The present invention is directed to a double band press for continuously pressing material in sheet form within a reaction zone between a pair of endless, heated press belts of a double band press at increased process temperatures.

The types of materials which are usually treated in devices of the type to which the present invention relates may comprise, for example, plastic material comprising bound laminates or fiber binding agent mixtures. In known devices of this type, the temperatures at which the materials can be pressed and to which they can be subjected are limited primarily by the thermal and oxidation stabilities, i.e., the resistance to heat and oxidation, of the lubricants in the press belts which are supported mechanically, for example, by means of roller members, or by means of thermal stability of the sealing materials and of the pressure means in hydraulically supported press belts. It is sometimes desired, for example, in compressing fiber binding agent mixtures, wherein the binding agents are thermoplastic materials with melting points between 250° and 350° C., to use press belt temperatures ranging up to approximately 40° C. above the temperature values mentioned. However, conventional lubricants and elastomer sealing materials withstand operating temperatures only up to approximately 200° C.

In the known double band presses, the heat is either transmitted to the intake or feed side of the press by means of heating of the deflecting drums on which the press bands are supported. Otherwise, it is transmitted to the inside of the press belts themselves by means of heating of a pressure plate, so that the press belts are supported in the area of the reaction zone, or also, by a hot pressure means. The heat flows from the inside of the press belts through the press belts at their outer side and is there imparted to the sheet material lying between the press belts.

Naturally, higher temperatures prevail at the inner sides of the press belts than at the outer sides thereof which contact the sheet material. This is in itself a technological contradiction because, at the inside of the press belt, the higher temperature damages the sealing means, pressure means or lubricants which are utilized, while, the lower temperatures at the outsides of the press belts are often not sufficient to produce the necessary binding reactions.

SUMMARY OF THE INVENTION

Accordingly, the present invention is directed toward apparatus which will make it possible to process sheet material in double band presses at press belt temperatures which are higher than would be permissible as operating temperatures in known devices of this type involving elements such as sealings, sliding materials, pressure means and lubricants.

In accordance with the invention, the press belts are heated in such a manner that they have the highest temperature at their outer sides which face the sheet material and the heat flow is effected through the press belt from this hot outer side to the opposite inner side of the press belt.

In accordance with the invention, in the vicinity of the press belt outer sides, shortly before the reaction zones in which the sheet material is treated and pressed, suitable heating means are provided which may comprise strip-shaped gas burners or electrical induction heating devices, with coupling coils through which pass high frequency alternating currents, the heating means being arranged to extend transversely over the width of the press belts.

The various features of novelty which characterize the invention are pointed out with particularity in the claims annexed to and forming a part of this disclosure. For a better understanding of the invention, its operating advantages and specific objects attained by its use, reference should be had to the drawings and descriptive matter in which there is illustrated and described a preferred embodiment of the invention.

DETAILED DESCRIPTION OF A PREFERRED EMBODIMENT

Figure 1:
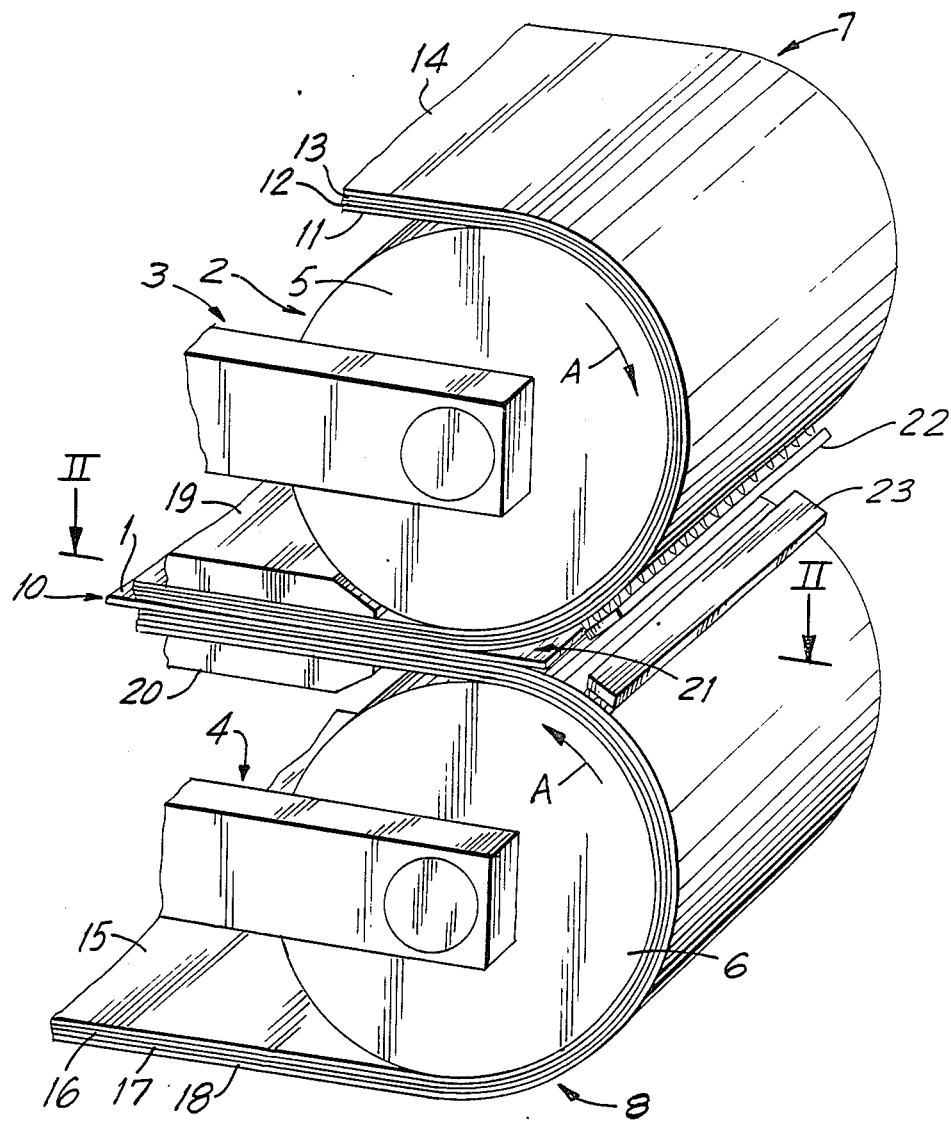
FIG. 1 is a perspective schematic representation showing the double band press with the duel heated press belts in accordance with the invention.

Referring now to FIG. 1, there is shown, in perspective, apparatus in accordance with the present invention. In FIG. 1, there is shown the intake zone of a double band press 2 which is utilized for hot pressing of a forwardly moving material sheet 1. The material sheet 1 can be a plastic material-bound laminate, e.g., an electrolaminate or also a fiber binding agent mixture, wherein the binding agent is a thermoplast with a melting point between, for example, 250° and 350° C.

In the area of the intake zone, the double band press 2 is formed with two deflecting drums 5 and 6 which are arranged one above the other and which are rotatably supported in bearing supports 3 and 4, respectively. An endless press belt 7 and 8 is respectively guided around each drum 5, 6. The press belts 7, 8 extend in a manner known per se over additional deflecting rollers (not shown) which are likewise supported on the bearing supports 3, 4.

Figure 2:
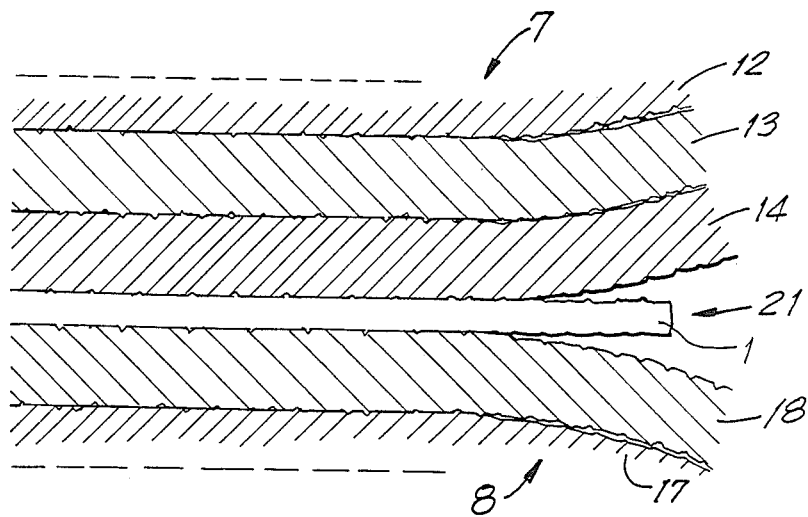
FIG. 2 is a sectional view taken along the line II—II of FIG. 1 showing parts of the apparatus on an enlarged scale.
Figure 3:
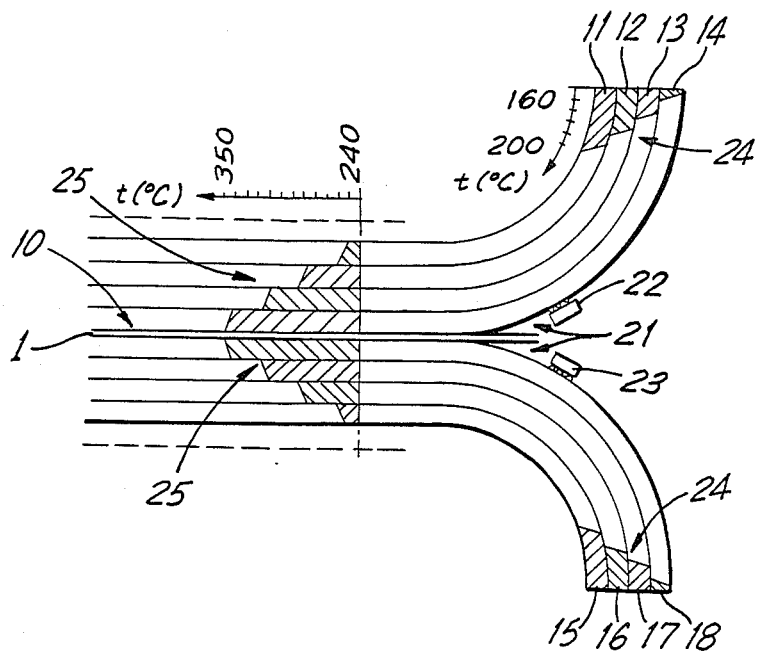
FIG. 3 is a schematic representation depicting the temperature curve in a press belt pack in front of and behind a heating zone.

As shown in the drawings and also in FIGS. 2 and 3, each press belt 7, 8 consists of a press belt pack which is formed in each instance from four belt sides or layers 11, 12, 13, and 14, in the case of the deflecting drum 5, and 15, 16, 17, and 18, in the case of the deflecting drum 6. The four sides of each of the press belt packs are pressed into one another.

The belt sides 14 and 18, respectively, comprise in each instance the outer side or surface of the individual press belt pack and they engage, respectively, on opposite sides of the material sheet 1 in the area of the reaction zone 10, as shown in FIG. 1. The rotating direction of the individual press belts is indicated by arrows A in FIG. 1. The material sheet 1 advances from right to left, as seen in FIG. 1, and is compressed in the reaction zone 10 accompanied by the simultaneous application of heat and pressure. The deflecting drums 5, 6 are heated in a manner known per se so that the heat is transferred from the drums to the multilayered press belts 7, 8.

The pressure to be exerted on the sheet material 1 is hydraulically or mechanically applied to the respective inner sides of the press belts 7, 8 in a known manner by means of pressure plates 19, 20 and is transmitted from there to the material sheet 1 over the individual belt positions. In hydraulic pressure transmission, a fluid pressure medium, which can be put under pressure, is brought into the space between the pressure plates 19, 20 and the rear side of the innermost belt side 11 or 15, respectively. This space is defined laterally by means of sealings (not shown) which consist, as a rule, of organic, elastomer sealing materials with only limited thermal stability. In pressure transmission, roller members which extend transversely over the press belt width are arranged in the intermediate space between the pressure plates 19, 20 and the rear side of the innermost belt side 11 or 15, respectively. The pressure plates, with the roller members, are pressed against the inner belt side by means of pressure cylinder means. The lubricants required for the roller members likewise have a limited decomposition or dissolution and oxidation stability at increased temperatures.

The reaction zone 10 between the press belts 7 and 8 is formed with an intake gap 21 and in an area as close as possible immediately before the intake gap 21, there are provided transverse heater means in the form of gas burners 22, 23 which emit flames acting directly on the outer side of the outer belt sheets or layers 14, 18, respectively. The heaters or burners 22, 23 extend transversely over the width of the press belt 7, 8.

As a result, the surfaces of the belt sides are heated shortly prior to entering the intake gap 21 in the area of a flame zone by means of the heat of the combustion gases of the heater means 22, 23, specifically at a temperature higher than that temperature to which the press belts are heated by the deflecting drums 5, 6.

Instead of gas burners 22, 23, there may also be utilized electrical induction heating devices with coupling coils through which high frequency alternating current is applied.

Before the circulating press belts 7, 8 reach the gas burners 22, 23, they are warmed by means of the heated deflecting drums 5, 6. As may be seen from the enlarged drawing shown in FIG. 2, in the area of the intake zone 21, prior thereto or in front thereof, a heat contact between the belt sides forming the press belts 7, 8 is only provided locally because of surface roughness, since the press belts are not yet subjected here to pressure. Accordingly, the heat resistance at this point is great and there is a decreasing heat gradient from the inner belt sides 11, 15, respectively, to the outer belt sides 14, 18, respectively. The temperature of the deflecting drums 5, 6 can be adjusted in such a way that the operating temperature permissible for the sealing materials, lubricants or the like, which is the so-called critical temperature, is not seated on the inner belt side.

The temperature gradient or descending gradient in the press belt packs in front of and behind the flame or heating zones formed by the gas burners 22, 23 is schematically shown in FIG. 3. The temperature gradient decreases in front of the flame area or zone is provided or identified with reference numeral 24 and the temperature gradient behind the flame zone is provided or identified with the reference numeral 25. The temperature of the inner belt sides 11, 15 is around 200° C., that is, beneath a critical temperature of, for example, 240° C. The highest levels of the temperatures in question is indicated in each instance by means of corresponding hatching at the corresponding belt sides, with reference to a temperature scale. The heat flows from the inner belt sides 11, 15 to the outer belt sides 14, 18, respectively, by means of heat conductance, wherein, however, a heat gradient or descending gradient is produced toward the outer belt sides because of the heat resistance and the temperature accordingly lies at around 160° C.

In the flame zones located in the area of the gas burners 22, 23, the heat flow direction reverses by means of the high heating of the outer belt sides 14, 18. In so doing, the temperature generated by means of the burners 22, 23 is selected in such a way on the outer belt side that it is optimal for the material sheet 1 to be processed. In so doing, the aforementioned critical temperature can be easily exceeded, since the temperature increase in the inner belt sides is negligible because of the poor heat conductivity of the belt sides lying loosely on top of one another.

In the area of the reaction zone, where the full pressure acts on the press belts 7, 8 by means of the pressure plates 19, 20, the heat resistance drops at the transitions between the individual belt sides since, as shown in FIG. 2, the heat transmission surface increases under the action or effect of the pressure. However, the major portion of the heat flow occurs from the outer belt sides 14, 18 which are additionally heated by means of the burners 22, 23 directly at their outer sides, to the directly adjoining material sheet 1 and leads in this sheet to the higher temperature desired there. Accordingly, the temperature decrease, designated in FIG. 3 by 25, is produced. The outer belt sides 14, 18, as is shown with the aid of the cross-hatching have a temperature of approximately 350° C., which is far above the critical temperature. On the other hand, in the belt sides of the press belts located further inwardly, the temperature decreases steadily and achieves a value at the innermost belt side 11, 15 which no longer exceeds the critical temperature of approximately 240° C.

The values shown in FIG. 3 depend on the respective materials and the operating parameters of the double band press. They can be adapted to the respective operating case. At any rate, in each instance, the desired high process temperature can be achieved in the area of the reaction zone at the outside of the outer press belt side while, at the insides of the inner belt sides, the critical temperature is not exceeded.

In a preferred form of the invention, the press belts are constructed in a multiple-layered manner as "press belt packs". However, the reversal of the heat flow in accordance with the invention described herein may also be achieved in double band presses with only single layer press belts. For this purpose, in single layer press belts, the surface of the deflecting drums on the intake side may be formed in a thermally insulating manner, for example, by means of a rubber coating. The heat transmission or transition surface can also be reduced in the direction toward the single layer press belt by means of knurling, grooving or the like of the surface of the deflecting drum. Shortly before the intake in the reaction zone, the single layer press belt is intensively heated, as described in the foregoing with regard to the multiple layer press belt, wherein considerable quantities of heat then no longer pass into the deflecting drums. Since several seconds pass before the heat has flowed from the belt surface to the rear of the belt and the flow of heat into the sealing members, supporting roller members or pressure means is hindered as a result of poor heat transmission to the material boundaries, the material sheet is successfully heated in each instance to temperatures which lie substantially above the critical values of the machine materials.

In multiple layer press belts, the heat transmission will improve suddenly as soon as the belt packs reach the reaction zone and arrive under high surface pressure. However, the heat transmission to the press belt inner sides which, accordingly, accompanies this and which is undesirable is limited by means of the intended heat absorption by the material sheet. Moreover, the boundary surfaces present in multiple layer press bands will naturally provide a characteristic whereby the heat transmission to the sensitive parts and materials on the inside of the machine will remain within boundaries.

The advantages which may be achieved by means of the present invention are primarily of an economic nature. According to the invention, the material sheets are continuously pressed and can be wound up on rollers. By means of this, a higher yield of up to 15% may be accomplished in accordance with cutting size in contrast to arc-shaped materials such as those which can be produced, for example, with the aid of single layer or multiple layer presses. Since high temperature-resistant material sheeting in the form of laminates or fiber binding agent mixtures, as a rule, require very expensive raw materials, the higher yield can offset the costs of the processing device in a very short time.

Many fiber binding agent mixtures are practically ideal heat insulators which could previously be brought to the required compression temperature only by means of convective heat transmission. Known presses of the multilayer or hydraulic type are suitable for this, but their heating plates require capacities of up to two orders of magnitude higher, which leads to a correspondingly higher energy consumption during the necessary recooling and high compression temperatures. Here again, the invention provides an improvement.

While a specific embodiment of the invention has been shown and described in detail to illustrate the application of the inventive principles, it will be understood that the invention may be embodied otherwise without departing from such principles.

What is claimed is:

1. A double band press for continuous pressing of material sheeting at increased process tempertures comprising: two endless heated press belts located one above the other and defining therebetween a reaction zone in which said material sheeting is pressed, each of said belts running over a different pair of deflecting drums with said deflecting drums mounted in a press stand, said reaction zone having an intake gap located at one end between one said deflecting drum of each said pair whereby the material sheeting to be pressed enters the intake gap where it is pressed under the action of area pressure and heat stored in the press belts, said press belts each consisting of a plurality of belt layers which are pressed directly one against another; said deflecting drums located at the intake gap being heated said press belts having an inner side contacting said deflecting drums and an outer side defining the reaction zone and contacting the material sheeting within the reaction zone, said deflecting drums at the intake gap operating to heat said press belts from the inner sides thereof located adjacent said drums before said belt layers reach said reaction zone to a temperature below a critical temperature determined by a maximum allowable operational temperature of the inner side of said press belts; and strip-shaped heater means extending transversely over a width of said press belts and arranged in the vicinity of the outer sides of said press belts, said outer sides being opposite said inner sides and being brought into contact with said material sheeting at the intake gap for the commencement of pressing the material sheeting in said reaction zone; said strip-shaped heater means being located shortly before the intake gap into said reaction zone and downstream of the location where the press belts contact the deflecting drums adjacent the intake gap and operating to heat said press belts in such a manner that said press belts are heated above the critical temperature and have their highest temperature at said outer sides facing said material sheeting with heat flow through said press belts being effected with high heat resistance from said hotter outer sides thereof toward said opposite inner sides of said press belts.

2. A double band press according to claim 1, wherein said strip-shaped heater means comprise gas burners.

3. A double band press according to claim 1, wherein said strip-shaped heater means comprise electrical conduction heating members with coupling coils through which high frequency alternating current is passed.

* * * * *